United States Patent [19]

Kappas et al.

[11] Patent Number: 4,619,923

[45] Date of Patent: Oct. 28, 1986

[54] METAL PROTOPORPHYRINS IN THE CONTROL OF TRYPTOPHAN METABOLISM

[75] Inventors: Attallah Kappas; George S. Drummond, both of New York, N.Y.

[73] Assignee: The Rockefeller University, New York, N.Y.

[21] Appl. No.: 691,460

[22] Filed: Jan. 14, 1985

[51] Int. Cl.$^4$ ............................................. A61K 31/555
[52] U.S. Cl. .................................... 514/185; 514/189; 514/836; 514/893
[58] Field of Search ................. 514/185, 189, 836, 893

[56] References Cited

U.S. PATENT DOCUMENTS

| | | | |
|---|---|---|---|
| 3,017,325 | 1/1962 | Vogel | 514/185 |
| 4,100,160 | 7/1978 | Walser | 514/893 |
| 4,352,814 | 10/1982 | Walser | 514/893 |
| 4,386,087 | 5/1983 | Lavallee | 514/185 |

OTHER PUBLICATIONS

The Merck Index, Cite No. 7800, 10th Ed. (1983).

Primary Examiner—Albert T. Meyers
Assistant Examiner—John M. Kilcoyne
Attorney, Agent, or Firm—Wyatt, Gerber Shoup, Scobey and Badie

[57] ABSTRACT

Method of controlling the rate of tryptophan metabolism in the liver of humans by parenteral administration of tin or chromium protoporphyrin to increase the rate, and the administration of cobalt protoporphyrin to decrease the rate.

3 Claims, 2 Drawing Figures

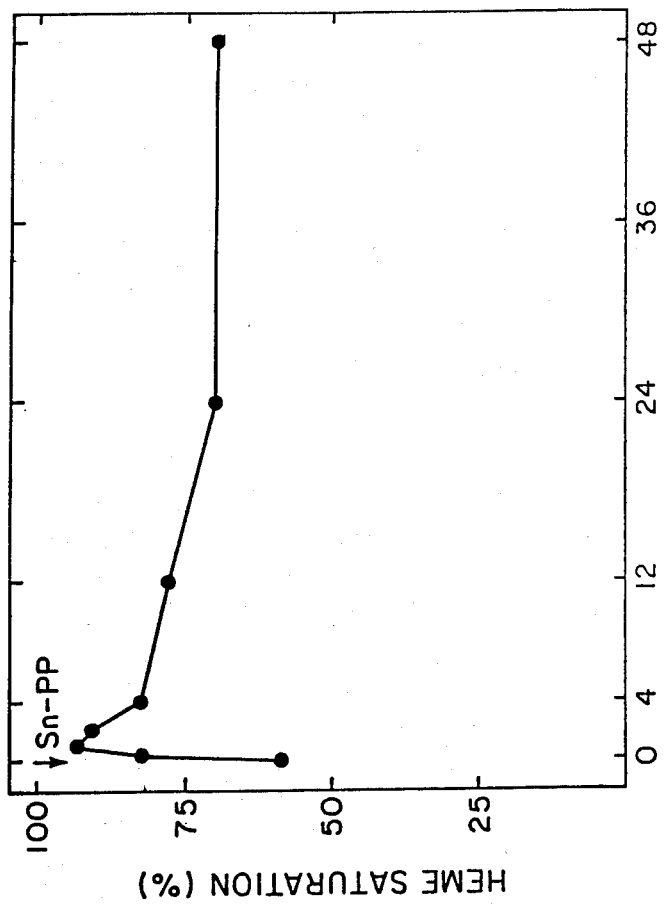

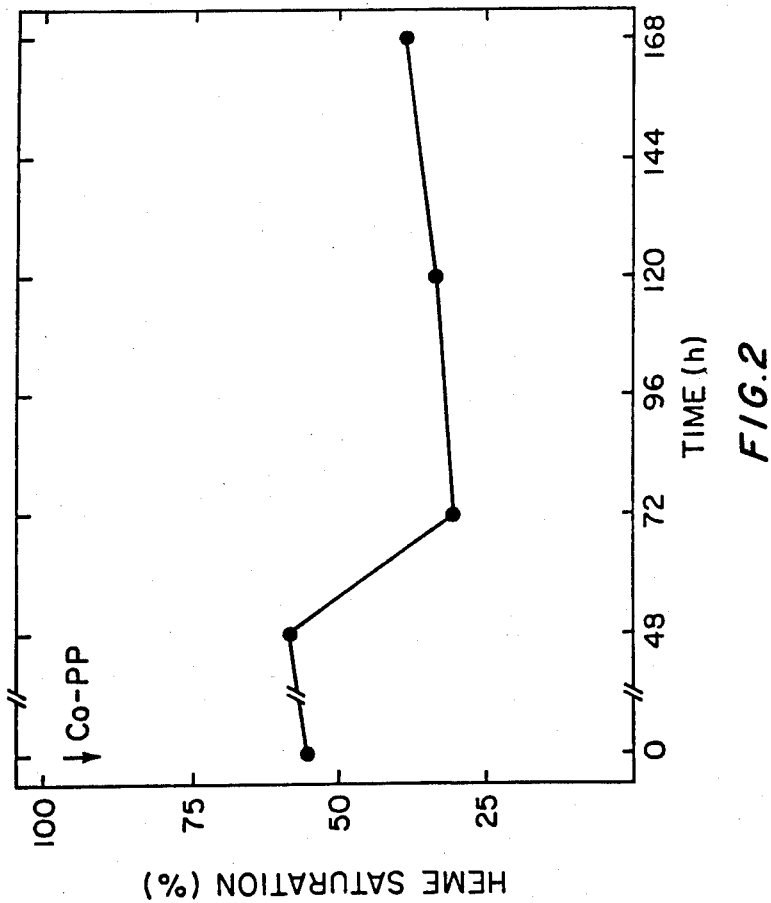

METAL PROTOPORPHYRINS IN THE CONTROL OF TRYPTOPHAN METABOLISM

This invention is concerned with methods of controlling the rate of tryptophan metabolism in the liver of humans in need of such control by the parenteral administration of effective amounts of metal protoporphyrins.

It has been discovered that the administration of tin or chromium protoporphyrin will increase the rate at which tryptophan is metabolized in the liver, and that the administration of cobalt protoporphyrin will decrease the rate.

Iron protoporphyrin, also called heme, or more accurately ferroprotoporphyrin IX, is the specific porphyrin isomer found in mammalian whole blood. It is an esential component in the respiratory chain and in energy transfer reactions which take place in the mammalian body. It is also a vital component of tryptophan pyrrolase, a liver enzyme whose activity is completely dependent on the extent to which it is combined (i.e., "saturated") with heme.

A number of synthetic analogs of iron protoporphyrin IX are known. They are commercially available or are readily synthesized by known methods. These include, for example, tin, chromium and cobalt protoporphyrins. For convenience herein, these compounds will be referred to generically as Me-PP, where Me stands for metal, and specifically by utilizing the chemical symbol for the metal such as Sn-PP, Cr-PP and Co-PP for the tin, chromium and cobalt compounds.

Tryptophan is an essential amino acid which has profound effects on a number of metabolic pathways in the whole animal, including man, particularly in the nervous system. Tryptophan is metabolized principally in the liver. Tryptophan which is not metabolized in the liver accumulates in the plasma and in the brain. Brain levels of tryptophan are dependent on plasma levels of the amino acid which in turn are regulated by liver tryptophan pyrrolase. Tryptophan in the brain is metabolized by a different route than in the liver. One of the principal metabolic protects of tryptophan in the brain is 5-hydroxytryptamine, or serotinin. The concentrations of tryptophan and serotinin in the brain are closely regulated in humans. Increased concentrations of these products are associated with hepatic encephalopathy and migrane headaches. Encephalopathy is a known afflication characterized by degenerative changes in the brain cells leading to confused states and other abnormal behavior patterns as well as convulsions, stupor and coma. Decreased concentrations of these products have been implicated in narcolepsy, depression and myoclonic disorders characterized by uncontrolled jerky movements.

Tryptophan pyrrolase is an enzyme which occurs in the liver of humans. It catalyzes the oxidative cleavage of tryptophan to N-formylkynurenine and is the first and rate-limiting enzyme in the catabolism of tryptophan in the liver. The active holoenzyme is normally about 50% saturated with heme, but fluctuations in the availability of cellular heme produce rapid changes in the enzyme activity by converting the inactive, heme-free apoenzyme to the active heme containing holoenzyme.

More specifically, an increase in the amount of heme in the liver as can be produced by parenteral administration of Me-PP such as Sn-PP or Cr-PP as a result of the ability of these compounds to block the catabolism of heme causes increased saturation of tryptophan pyrrolase with heme. The heme-saturated tryptophan pyrrolase is the active form of the enzyme. The incresed activity of the enzyme resulting from its increased saturation with heme causes an increased rate of tryptophan metabolism in the liver. As a result there is less spillover of intact tryptophan into the plasma and, ultimately, less accumulation of tryptophan and serotonin in the brain.

The opposite result is effected by administration of Co-PP. There is a decrease in available heme in the liver (because Co-PP enhances the rate of heme degradation in liver), a decrease in the activity of tryptophan pyrrolase, and an increase in the amount of intact tryptophan and serotonin in the brain.

FIG. 1 shows the changes in liver tryptophan pyrrolase activity resulting from parenteral administration of Sn-PP to rats. In this study Sn-PP was administered subcutaneously at a dosage level of 10 $\mu$mol/kg of body weight to male Sprague-Dawley rats (108–200 g). Control animals received an equivalent volume of aqueous isotonic saline. Tissue preparation of liver fractions for enzymic assays were conducted as described by Drummond and Kappas. Proc. Natl. Acad. Sci. USA. 78:6466–6470 (1981). Tryptophan pyrrolase activity was determined both in the absence (holoenzyme) and the presence (total enzyme) of added heme (2 $\mu$m). The latter enzyme activity was calculated from the linear phase of kynurenine formation. The percent heme saturation for tryptophan pyrrolase was expressed as the ratio of holoenzyme to total enzyme ($\times 100$). Each data point in the figure represents the mean value of determinations in 3 to 6 animals.

It will be noted that the injection of the selected dose of Sn-PP caused a marked and rapid increase in the percent heme saturation and resulting tryptophan pyrrolase activity, reaching nearly 100% saturation in one to two hours and being maintained at an increased level for up to 72 hours. With Cr-PP, a maximum saturation of about 80% was reached in about two hours, and the increased level was maintained for up to 24 hours.

FIG. 2 shows the result of subcutaneous administration of Co-PP to similar Sprague-Dawley rats. It will be observed that Co-PP effected, after a latent period, substantial decrease in heme saturation of tryptophan pyrrolase to levels of ~25% beginning at 48 hours after administration and that the effect of this single dose of Co-PP was maintained for at least120 hours.

The results reported in the figures clearly establish the ability of the selected Me-PP to control tryptophan pyrrolase activity and thereby control the rate of tryptophan metabolism in the liver.

The threapeutic agents of this invention will be administered parenterally in dosage quantities which may vary over a relatively wide range depending upon the many factors which the attending physician can readily evaluate including, for example, the condition being treated, whether the condition is acute or chronic and the age, weight and general health of the patient. Normally a dosage of from 5 to 25 mg/kg of body weight will be effective. Any of the usual parenteral routes may be employed, but subcutaneous injection is preferred. One dosage may be sufficient, or a series of dosage units may be administered at suitable time intervals.

In order to have appropriate dosage units available, compositions containing the Me-PP of this invention will normally be prepared in bulk at concentrations of from 2 to 25 grams per liter subdivided into dosage units containing approximately 2 to 25 milligrams per milliliter of solution.

Any of a number of pharmaceutical carriers may be employed including, for example, isotonic aqueous salt or glucose solutions buffered to a pH of about 7.4.

As will be clear from the foregoing, the Me-PPs of this invention because of their ability to increase or decrease the rate at which tryptophan is metabolized in liver are useful in the treatment of a number of human ailments associtaed with variations in tryptophan and serotonin concentration in the brain. These include, for example, hepatic encephalopathy, manic-depressive disorder, narcolepsy, migrane headaches, and myoclonic diseases.

What is claimed is:

1. A method of increasing the rate of tryptophan metabolism in the liver of humans in need of such increase which comprises parenteral administration of an amount of tin protoporphyrin which is effective to increase such rate.

2. A method of increasing the rate of tryptophan metabolism in the liver of humans in need of such increase which comprises parenteral administration of an amount of chromium protoporphyrin which is effective to increase such rate.

3. A method of decreasing the rate of tryptophan metabolism in the liver of humans in need of such decrease which comprises parenteral administration of an amount or cobalt protoporphyrin which is effective to decrease such rate.

* * * * *